(12) United States Patent
Homann et al.

(10) Patent No.: US 11,141,123 B2
(45) Date of Patent: Oct. 12, 2021

(54) FRACTIONAL FLOW RESERVE DETERMINATION

(71) Applicant: Koninklijke Philips N.V., Eindhoven (NL)

(72) Inventors: Hanno Heyke Homann, Eindhoven (NL); Michael Grass, Eindhoven (NL); Raoul Florent, Eindhoven (NL); Holger Schmitt, Eindoven (NL); Odile Bonnefous, Eindhoven (NL); Hannes Nickisch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 275 days.

(21) Appl. No.: 15/532,968

(22) PCT Filed: Dec. 1, 2015

(86) PCT No.: PCT/EP2015/078117
§ 371 (c)(1),
(2) Date: Jun. 2, 2017

(87) PCT Pub. No.: WO2016/087396
PCT Pub. Date: Jun. 9, 2016

(65) Prior Publication Data
US 2019/0083052 A1 Mar. 21, 2019

(30) Foreign Application Priority Data
Dec. 2, 2014 (EP) ..................................... 14306939

(51) Int. Cl.
*A61B 6/00* (2006.01)
*A61M 5/00* (2006.01)
(Continued)

(52) U.S. Cl.
CPC .............. *A61B 6/507* (2013.01); *A61B 6/466* (2013.01); *A61B 6/481* (2013.01); *A61B 6/486* (2013.01);
(Continued)

(58) Field of Classification Search
CPC combination set(s) only.
See application file for complete search history.

(56) References Cited

U.S. PATENT DOCUMENTS

| 8,157,742 B2 | 4/2012 | Taylor |
| 8,670,943 B2 | 3/2014 | Kassab et al. |

(Continued)

FOREIGN PATENT DOCUMENTS

| EP | 2026276 A2 | 2/2009 |
| JP | 2000232611 A | 8/2000 |

(Continued)

OTHER PUBLICATIONS

Wil Reddinger, CT Physics Registry Review, Imaging Education Associates, www.aheconline.com/mktg/course_materials/CTPrepExam/2-CTPrepExam.pdf (Year: 2007).*

(Continued)

*Primary Examiner* — Joanne M Hoffman
*Assistant Examiner* — Alexei Bykhovski (57) ABSTRACT

The present invention relates to a device (1) for fractional flow reserve determination. The device (1) comprises a model generator (10) configured to generate a three-dimensional model (3DM) of a portion of an imaged vascular vessel tree (VVT) surrounding a stenosed vessel segment (SVS), based on a partial segmentation of the imaged vascular vessel tree (VVT). Further, the device comprises an image processor (20) configured to calculate a blood flow (Q) through the stenosed vessel segment (SVS) based on an analysis of a time-series of X-ray images of the vascular (Continued)

vessel tree (VVT). Still further, the device comprises a fractional-flow-reserve determiner (30) configured to determine a fractional flow reserve (FFR) based on the three-dimensional model (3DM) and the calculated blood flow.

18 Claims, 7 Drawing Sheets

(51) Int. Cl.

| | | |
|---|---|---|
| *G06T 7/00* | (2017.01) | |
| *G06T 7/254* | (2017.01) | |
| *G16H 30/40* | (2018.01) | |
| *G16H 50/50* | (2018.01) | |
| *A61B 6/03* | (2006.01) | |
| *A61B 5/026* | (2006.01) | |

(52) U.S. Cl.
CPC ............ *A61B 6/504* (2013.01); *A61B 6/5217* (2013.01); *A61B 6/582* (2013.01); *A61M 5/007* (2013.01); *G06T 7/0016* (2013.01); *G06T 7/254* (2017.01); *G16H 30/40* (2018.01); *G16H 50/50* (2018.01); *A61B 5/0263* (2013.01); *A61B 6/032* (2013.01); *A61B 6/482* (2013.01); *A61B 6/5258* (2013.01); *G06T 2207/10081* (2013.01); *G06T 2207/10088* (2013.01); *G06T 2207/10116* (2013.01); *G06T 2207/20224* (2013.01); *G06T 2207/30101* (2013.01); *G06T 2207/30104* (2013.01)

(56) References Cited

U.S. PATENT DOCUMENTS

| | | | | |
|---|---|---|---|---|
| 2002/0025267 A1* | 2/2002 | Lieber | ................ | A61M 5/1452 |
| | | | | 417/572 |
| 2011/0282586 A1* | 11/2011 | Kassab | .............. | A61B 5/02007 |
| | | | | 702/19 |
| 2012/0041318 A1* | 2/2012 | Taylor | ................ | A61B 5/02007 |
| | | | | 600/504 |
| 2013/0060133 A1* | 3/2013 | Kassab | .................. | A61B 6/504 |
| | | | | 600/431 |
| 2014/0024932 A1* | 1/2014 | Sharma | .................. | A61B 6/507 |
| | | | | 600/431 |
| 2014/0086461 A1* | 3/2014 | Yao | ....................... | G06T 7/0016 |
| | | | | 382/128 |
| 2014/0088414 A1 | 3/2014 | Mittal et al. | | |
| 2014/0114185 A1 | 4/2014 | Tolkowsky | | |
| 2014/0121513 A1 | 5/2014 | Tolkowsky | | |
| 2014/0243662 A1* | 8/2014 | Mittal | .................... | A61B 6/481 |
| | | | | 600/425 |
| 2015/0025370 A1* | 1/2015 | Neukirchen | ........... | A61B 6/032 |
| | | | | 600/425 |
| 2015/0071520 A1* | 3/2015 | Takemoto | .............. | A61B 6/481 |
| | | | | 382/132 |
| 2016/0278725 A1* | 9/2016 | Van Nijnatten | ........ | A61B 6/481 |

FOREIGN PATENT DOCUMENTS

| | | | |
|---|---|---|---|
| WO | 20130138428 A1 | 9/2013 | |
| WO | 20130183775 A1 | 12/2013 | |
| WO | 2014111927 A1 | 7/2014 | |
| WO | 2014072861 A2 | 9/2014 | |

OTHER PUBLICATIONS

Pijls et al. Circulation 87 (1993) pp. 1354-1367 "Experimental basis of determining maximum coronary, myocardial, and collateral blood flow by pressure measurements for assessing functional stenosis severity before and after percutaneous transluminal coronary angioplasty."

Koo et al. Cardiac Imaging 58 (2011) pp. 1989-1997 "Diagnosis of lschemia-Causing Coronary Stenoses by Noninvasive Fractional Flow Reserve Computed From Coronary Computed Tomographic Angiograms."

Huo and Kassab, Journal of the Royal So 9 (2012), pp. 190-200: "Intraspecific scaling laws of vascular trees."

Meuwissen et al. Circulation 106 (2002), pp. 441-446: "Hyperemic stenosis resistance index for evaluation of functional coronary lesion severity."

Pijls et al. "Percutaneous coronary intervention of functionally nonsignificant stenosis: 5-year follow-up of the DEFER Study." J Am Coll Cardiol 49, pp. 2105-2011 (2007).

Taylor et al. "Computational Fluid Dynamics Applied to Cardiac Computed Tomography for Noninvasive Quantification of Fractional Flow Reserve." JACC 61(22), pp. 2233-2241 (2013).

Wong, Molloi, et al. "Quantification of fractional flow reserve based on angiographic image data." Int J. Cardiovasc Imaging 28, pp. 13-22 (2012).

\* cited by examiner

FRACTIONAL FLOW RESERVE DETERMINATION

CROSS-REFERENCE TO PRIOR APPLICATIONS

This application is a U.S. National Phase application under 35 U.S.C. § 371 of International Application No. PCT/EP2015/078117 filed on Dec. 1, 2015, which claims the benefit of European Patent Application No. 14306939.1, filed on Dec. 2, 2014. These applications are hereby incorporated by reference herein.

FIELD OF THE INVENTION

The present invention relates to the field of coronary angiography. In particular, the present invention relates to a device and a method for fractional flow reserve determination.

BACKGROUND OF THE INVENTION

Coronary angiography allows for excellent visualization of coronary arteries. However, assessment of functional stenosis severity is limited. Fractional flow reserve, FFR, is a reliable measure for grading stenosis. Based on the aortic pressure $P_a$ and the pressure $P_d$ distal total stenosis, FFR is defined as: $FFR=P_d/P_a$.

Recently, the so-called virtual FFR method is receiving increasing interest for replacing the invasive pressure measurements by computational fluid dynamics simulation. This method is based on a geometric model of the coronary tree, which can be obtained either from computer-aided tomography angiography or from X-ray angiography images.

To evaluate the hemodynamic severity of coronary stenosis is a critical task in planning of cardiac interventions. Traditionally, the local reduction of the vessel diameter at the stenosis is assessed visually on cardiac images for this purpose.

U.S. Pat. No. 8,157,742 B2 describes a system for planning treatment for a patient. The system may include at least one computer system configured to receive patient-specific data regarding a geometry of an anatomical structure of the patient, create a three-dimensional model representing at least a portion of the anatomical structure of the patient based on the patient-specific data, and determine a first fractional flow reserve within the anatomical structure of the patient based on the three-dimensional model and a physics-based model relating to the anatomical structure of the patient.

WO 2014/072861 A2 describes methods and systems for fractional flow reserve calculations, wherein classifying of an unknown fractional flow reserve metric for a cardiac vessel with a stenosis as one of a plurality of different pre-defined classes based on extracted features and a learning model is performed.

SUMMARY OF THE INVENTION

There may be a need to improve devices and methods for fractional flow reserve determination.

This is met by the subject-matter of the independent claims. Further exemplary embodiments are evident from the dependent claims and the following description.

A first aspect of the present invention relates to a device for fractional flow reserve determination. The device comprises a model generator, which is configured to generate a three-dimensional model of a portion of an imaged vascular vessel tree surrounding a stenosed vessel segment, based on a partial segmentation of the imaged vascular vessel tree. Further, the device comprises an image processor, which is configured to calculate a blood flow through the stenosed vessel segment based on an analysis of a time-series of X-ray images of the vascular vessel tree. Still further, the device comprises a fractional-flow-reserve determiner, which is configured to determine a fractional flow reserve based on the three-dimensional model and the calculated blood flow.

The imaged vascular vessel tree may be modeled by creating a three-dimensional model representing at least a portion of the vascular vessel tree of a patient.

The present invention is based on a combination of the fractional flow reserve simulation with flow velocity measurements from angiographic images. For example, the flow velocity measurements may be based on an analysis, for example on an image processing analysis such as an image brightness analysis or an intensity analysis or contrast analysis.

The present invention advantageously improves the reliability of the boundary conditions of the simulated fractional flow reserve, since an accurate determination of the fractional flow reserve is provided. Further, the present invention advantageously reduces the geometric modeling requirements, since a blood flow through the stenosed vessel segment can be calculated with improved precision.

The present invention advantageously provides a combination of fractional flow reserve simulations with flow velocity measurements from a series of X-ray images, in particular angiographic images. A region of interest is marked in a first angiographic image and tracked over time in the subsequent images of the series following an injection of a contrast agent.

For example, by integrating the calibrated image intensities over the region of interest, the volumetric flow Q can be calculated as the slope of the time intensity curve at the time of arrival of the contrast bolus. Further, the aortic pressure is measured using known techniques as an inlet boundary condition.

For example, the present invention advantageously uses deriving the blood flow through the stenosis from a series of X-ray images and measuring the aortic pressure in order to calculate a corrected fractional flow reserve.

The present invention advantageously allows calculating, for example, the distal pressure at the stenosis from the determined FFR and a measurement of the aortic pressure.

According to a further, second aspect of the present invention, a medical imaging system is provided comprising a display device and a device according to the first aspect of the present invention or according to any implementation form of the first aspect of the present invention. The display device is configured to display the determined fractional flow reserve.

According to a further, third aspect of the present invention, a method for fractional flow reserve determination is provided, the method comprising the steps of:

a) generating a three-dimensional model of an imaged vascular vessel tree based on a partial segmentation of an imaged vascular vessel tree surrounding a stenosed vessel segment by a model generator;

b) calculating a blood flow through the stenosed vessel segment based on an analysis of a time-series of X-ray images by an image processor; and c) determining a fractional flow reserve based on the three-dimensional model of the imaged vascular vessel tree and the calculated blood flow by a fractional-flow-reserve determiner.

According to an exemplary embodiment of the present invention, the image processor is configured to conduct the analysis of the time-series of X-ray images within a period of up to 12 s, preferably of up to 5 s, most preferably of up to 1 s. This advantageously provides a temporal evaluation of the blood flow through the stenosed vessel.

According to an exemplary embodiment of the present invention, the device further comprises a controllable injector configured to provide a predefined flow profile of a contrast agent injected into the vascular vessel tree. This advantageously provides a reliable and normalized blood flow detection and analysis.

According to an exemplary embodiment of the present invention, the image processor is configured to perform a brightness calibration prior to the analysis of the time-series of X-ray images. This advantageously improves the accuracy of the blood flow detection and measurement.

According to an exemplary embodiment of the present invention, the image processor is configured to perform the brightness calibration by top-hat filtering or by image filtering or by bone removal or by digital subtraction of a reference image in at least one image of the time-series of X-ray images or in an image recorded prior to the recording of the time-series of X-ray images. The image filtering may refer to a preprocessing or filtering technique which improves the brightness analysis. This could also be dual energy angiography or angiography using a spectral detector which enables accurate iodine quantification.

In an example, the image processor is configured to calculate the blood flow using calibrated intensities over a region of interest including the stenosed vessel segment. This advantageously improves the accuracy of the blood flow detection and measurement.

According to an exemplary embodiment of the present invention, the image processor is configured to calculate the blood flow using a slope of a plot of the calibrated intensities as a function of integration time. This advantageously also improves the accuracy of the blood flow detection and measurement.

According to an exemplary embodiment of the present invention, the fractional-flow-reserve determiner is configured to calculate the fractional flow reserve using at least one boundary condition on an inlet and/or an outlet of the imaged vascular vessel tree. Advantageously, this improves the accuracy of the blood flow detection and measurement, too.

According to an exemplary embodiment of the present invention, the fractional-flow-reserve determiner is configured to use as the at least one boundary condition a pressure flow or flow constraint or a lumped element model composed of a resistor, a non-linear resistor or a capacitor. Improving the accuracy of the blood flow detection and measurement is advantageously also achieved.

The term "lumped element model" as used by the present invention refers to a parameter model that simplifies the description of the behavior of spatially distributed physical systems into a topology consisting of discrete entities that approximate the behavior of the distributed system under certain assumptions.

According to an exemplary embodiment of the present invention, the fractional-flow-reserve determiner is configured to adjust the at least one boundary condition to a determined diameter of a vessel of the imaged vascular vessel tree. This advantageously improves the accuracy of the blood flow detection and measurement.

According to an exemplary embodiment of the present invention, the fractional-flow-reserve determiner is configured to calculate a distal pressure of the stenosed vessel segment using a three-dimensional fluid dynamics simulation or a lumped components model, wherein a resistance of the stenosed vessel segment is approximated from a cross-sectional area of the stenosed vessel segment. This advantageously provides a reliable and normalized blood flow detection and analysis.

According to an exemplary embodiment of the present invention, the model generator is configured to generate the three-dimensional model of the portion of the imaged vascular vessel tree based on a portion of the vascular vessel tree distal to the stenosed vessel segment.

These and other aspects of the present invention will become apparent from and be elucidated with reference to the embodiments described hereinafter.

BRIEF DESCRIPTION OF THE DRAWINGS

A more complete appreciation of the present invention and the attendant advantages thereof will be more clearly understood with reference to the following schematic drawings, which are not to scale, wherein.

DETAILED DESCRIPTION OF EMBODIMENTS

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

Figure 1:
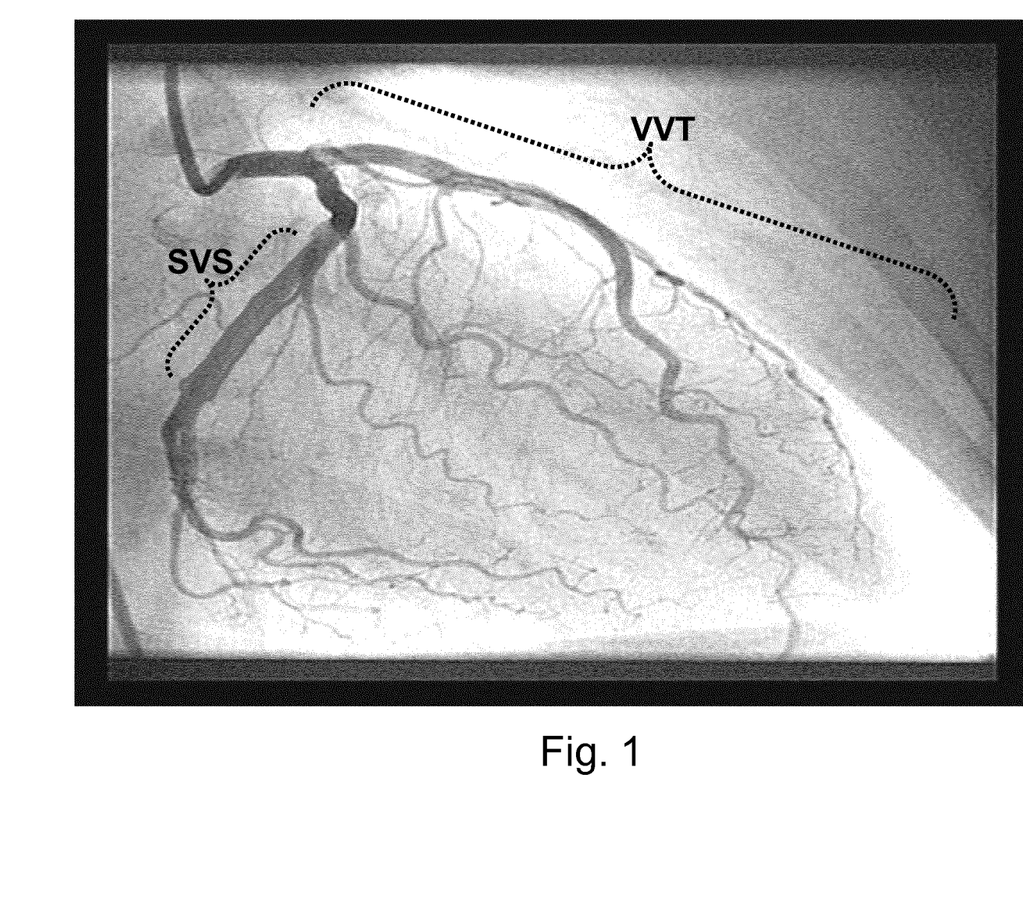
FIG. 1 shows a schematic diagram of region of interest on an image vascular vessel tree for explaining the present invention.

FIG. 1 shows a schematic diagram of a region of interest on an image vascular vessel tree for explaining the present invention.

In FIG. 1, an imaged vascular vessel tree VVT is shown and a partial segmentation of the image vascular vessel tree VVT is performed around a stenosed vessel segment SVS of interest.

According to an exemplary embodiment of the present invention, the geometric model of the coronary tree can be obtained by segmentation of cardiac computed tomography, CT, image volumes or from a few preferably two orthogonal X-ray angiography projections.

A quantitative measurement of the blood flow in the stenosed segment may be performed. For example, a densitometric approach may be suited to estimate the flow from a short time-series of X-ray angiography images.

A power injector, or a controllable injector, e.g. an injector module, can be used to minimize the dilution of the contrast agent with blood. For quantitative measurement of the contrast agent inflow, the image may be calibrated properly. To this end, scatter and background structures may be removed (e.g. by top-hat filtering, bone removal or by digital subtraction of a reference image) and the imaged intensity may be calibrated (e.g. using a phantom with known attenuation or using information of the three-dimensional vessel geometry). A region of interest, ROI, may be marked, as illustrated later on in FIG. 3, and tracked over time.

Figure 2:
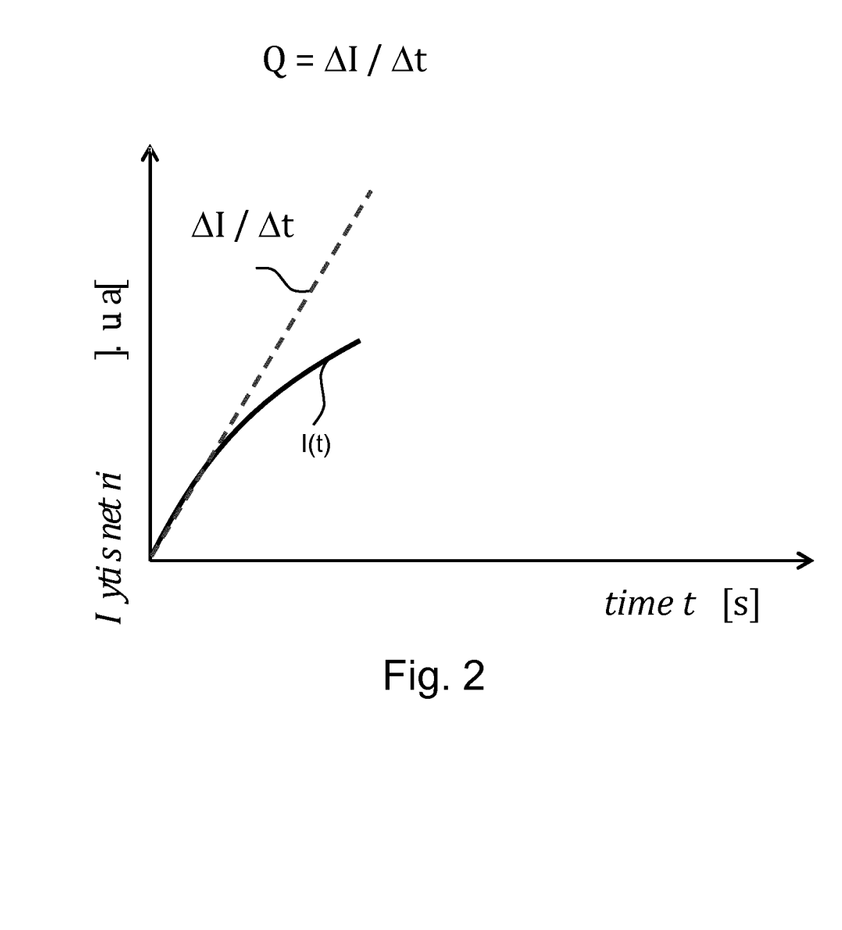
FIG. 2 shows a schematic diagram of an intensity as a function of time plot for explaining the present invention.

FIG. 2 shows a schematic diagram of an intensity as a function of time plot for explaining the present invention. According to an exemplary embodiment of the present invention, when integrating the calibrated intensities over the ROI, the volumetric blood flow Q can be calculated as the slope of the curve at bolus arrival time as shown in FIG. 2. Contrast transit-time or arrival-time methods for flow quantification might also be used, either as an alternative or in combination with the densitometric approach.

According to an exemplary embodiment of the present invention, as an inlet boundary condition, the aortic pressure can be estimated from arm cuff pressure measurements, or can be measured directly using an aortic catheter, as usually done in interventional cardiology. Using the flow boundary condition, the requirements for geometric modeling are significantly relaxed. A typical fractional flow reserve FFR simulation may be given by a detailed segmentation of the complete coronary tree (including fine distal branches).

Figure 3:
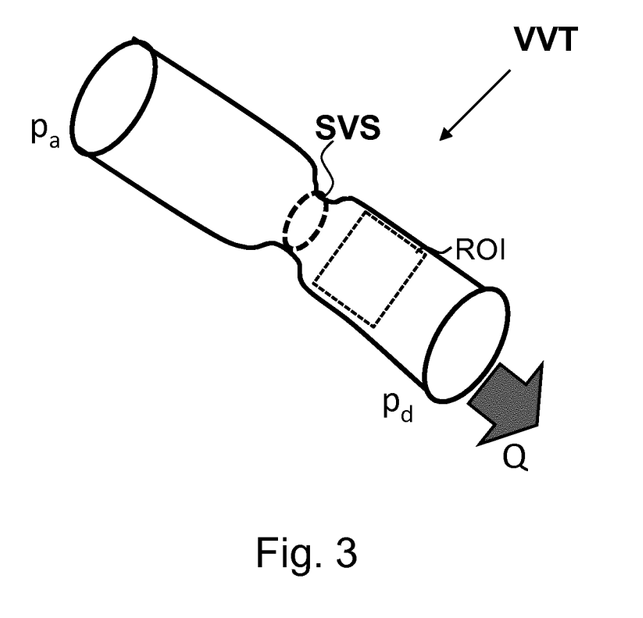
FIG. 3 shows a schematic diagram of a simple geometric model of a stenosed vessel segment for explaining the present invention.

FIG. 3 shows a schematic diagram of a simple geometric model of a stenosed vessel segment for explaining the present invention. FIG. 3 shows a partial segmentation of the image vascular vessel tree VVT around the stenosed vessel segment SVS.

According to an exemplary embodiment of the present invention, if the blood flow Q through the stenosis and the aortic pressure $p_a$ are known, a model of the stenosed vessel segment alone (as shown in FIG. 3) is sufficient to calculate the distal pressure $p_d$. This can be achieved via a full three-dimensional computational fluid dynamics simulation or by a lumped components approach where the segment's resistance is approximated from its cross-sectional areas, considering the Poiseuille effect (or Poiseuille's Law), the Bernoulli principle and others. Then, the fractional flow reserve FFR can be calculated as in the following equation:

$$FFR = P_d/P_a.$$

FIG. 3 shows a simple geometric model of a stenosed vessel segment. The inlet and outlet boundary conditions are given by the aortic pressure $p_a$ and the flow Q, respectively.

According to an exemplary embodiment of the present invention, the so-called virtual fractional flow reserve (vFFR) method may be used in combination with invasive pressure measurements by computational fluid dynamics (CFD) simulations. CFD simulations may be based on a geometric model of the coronary tree, which can be obtained either from CT angiography or from X-ray angiography images. A region of interest, ROI, may be marked and tracked over time.

Figure 4:
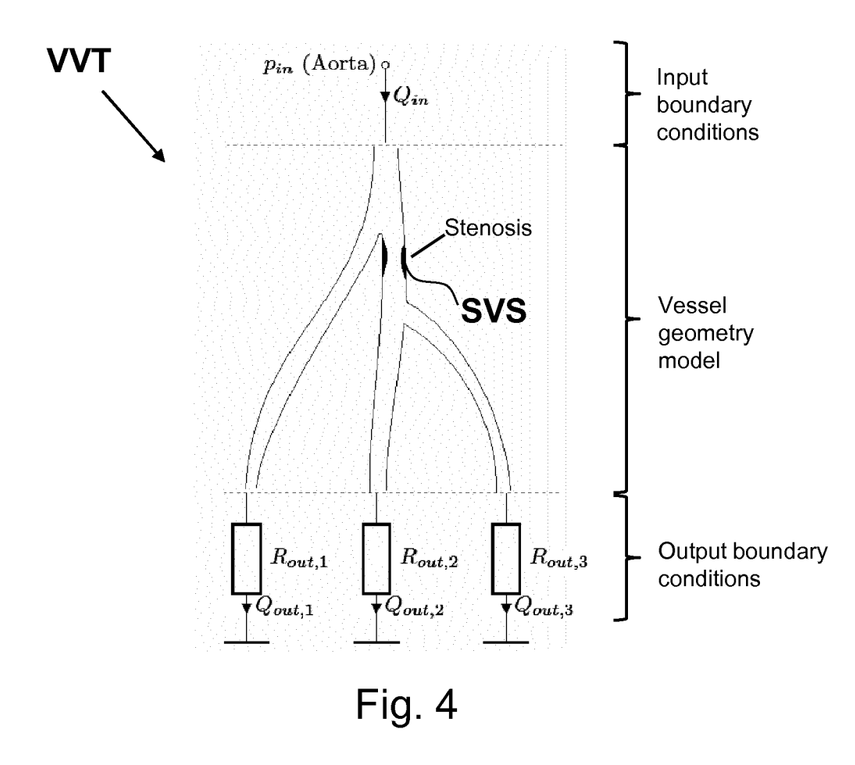
FIG. 4 shows a schematic diagram of a coronary vessel tree with typical boundary conditions for explaining the present invention.

FIG. 4 shows a schematic diagram of a coronary vessel tree with typical boundary conditions for explaining the present invention.

For accurate vFFR simulations, the choice of personalized boundary conditions at the inlets and outlets (as illustrated using FIG. 4) are considered. At each inlet and outlet, boundary conditions are assigned for non-ambiguous definition of all model variables. In general, these boundary conditions are pressure or flow constraints or lumped element models, composed of resistors, non-linear resistors (varistors) and dynamic elements (such as capacitors). For example, one can impose a pressure pin at the inlet (coronary ostium) and a particular resistance going to ground to each of the outlets.

The term "varistor" as used by the present invention refers to an electronic component with a nonlinear current-voltage characteristic, which is therefore also known as a voltage-dependent resistor (VDR).

The error of vFFR simulations depends at least linearly on a correct estimate of the flow value through the stenosis and hence on the correct choice of boundary conditions. If parts of the coronary tree are excluded from the segmentation, the flow through the remaining branches (especially through the stenosed segment) and hence the vFFR prediction would be compromised.

Figure 5:
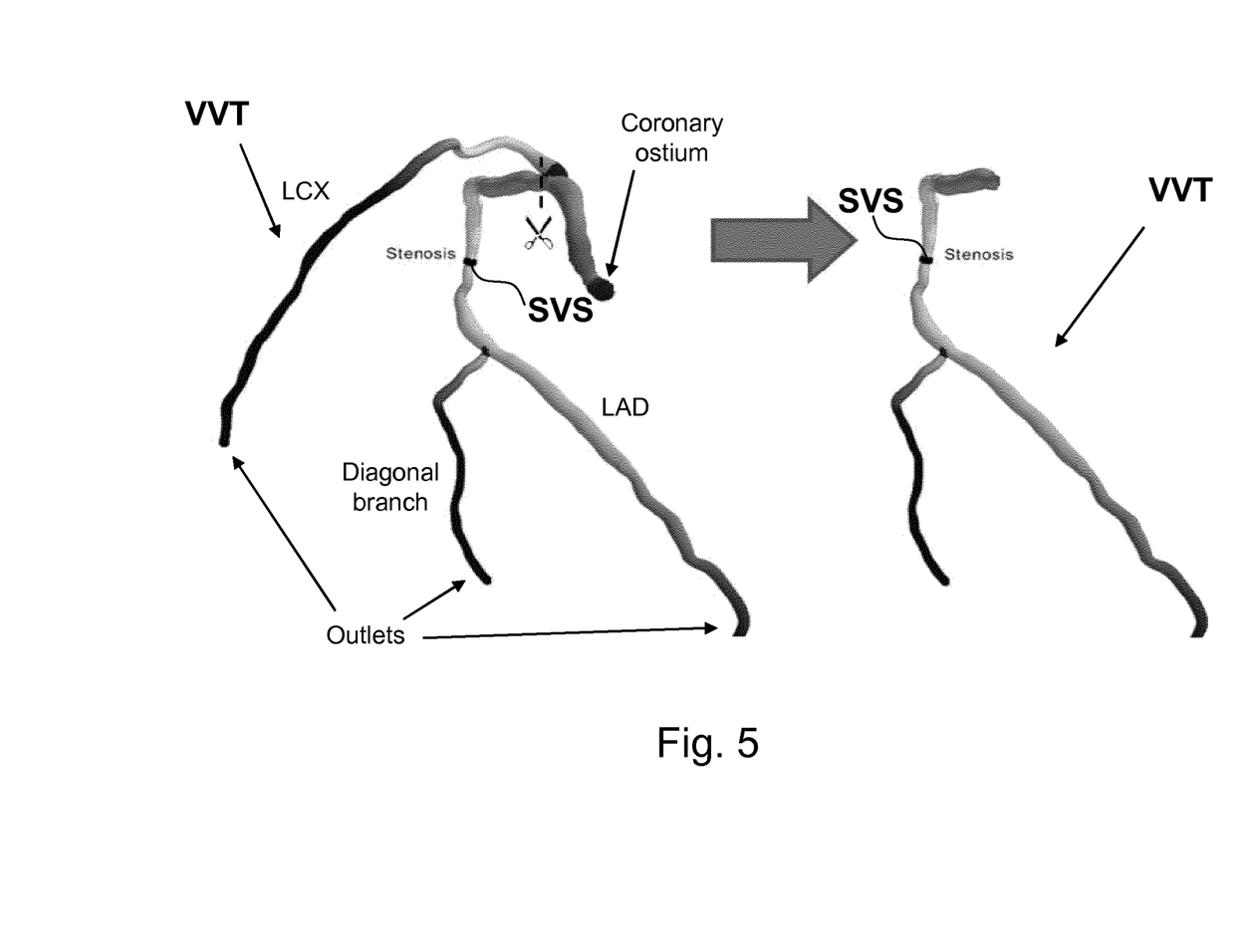
FIG. 5 shows a schematic diagram of a complete segmentation of the coronary vessels and the proposed reduced segmentation for explaining the present invention.

FIG. 5 shows a schematic diagram of a complete segmentation of the coronary vessels and the proposed reduced segmentation.

According to an exemplary embodiment of the present invention, the boundary conditions (pressures or resistances) at each outlet usually depend on the size (e.g. diameter, cross-sectional area) of the out-going vessel relative to the root vessel (e.g. LCA, RCA). Then, scaling laws can be applied to calculate the relative flow or impedance of each outlet. E.g. in case of a simple outlet resistance, resulting in equation 1:

$$R_{out} = 150 \frac{Pa}{m/s} \cdot \sqrt[3]{\frac{d_{root}}{d_{out}}}$$

wherein $R_{out}$ is the outlet resistance, $d_{out}$ is the diameter of the outlet, $d_{root}$ is the diameter of the root vessel, wherein the expression "Pa" of equation 1 refers to pascal (symbol: Pa) and is the SI derived unit of pressure, internal pressure, stress, Young's modulus and tensile strength, defined as one newton per square meter. The expression "m/s" of equation 1 refers to meter per second. Meter per second is an SI derived unit of speed (scalar) and velocity (vector), defined by distance in meters divided by time in seconds. Calculating the outlet resistance requires knowledge of the diameter $d_{root}$ of the root vessel, which is not available with an incomplete segmentation.

According to an exemplary embodiment of the present invention, it is proposed to calculate vFFR with only a partial segmentation of the vascular tree together with an explicit measurement of the diameter of the coronary ostium. This measure may be then used in a scaling law for the boundary conditions, e.g. as $d_{root}$ in equation 1.

The basic principle is illustrated in FIG. 5. Conventionally, a complete segmentation of the coronary vessel tree is preferred to increase the accuracy of vFFR calculations. A detailed segmentation, however, may be tedious and may hamper clinical workflow, especially during cardiac interventions. As the fractional flow reserve (FFR) value depends mostly on the stenosis geometry and the flow through the stenosed vessel segment, a partial segmentation (e.g. of the branches distal to the stenosis) can be sufficient for vFFR calculations if the ostium diameter is used to calculate peripheral resistance, for example by equation 1.

FIG. 5 shows a complete segmentation of the coronary vessel tree (left) and proposed reduced segmentation (right).

According to an exemplary embodiment of the present invention, the ostium diameter can be obtained (a) by interactive or (semi-)automated measurement on X-ray images or CT-volumes or (b) approximated by the diameter of coronary catheter, which was chosen by the interventional radiologist.

In general, it will often be reasonable to exclude the major branches located proximal to a stenosis from the segmentation (as in FIG. 5) without introducing a large error. This is true if the pressure drop Dp from the inlet to the cropping point is small, i.e. no stenosis is located there. This is not very limiting, because if stenoses were located there, this branches would be included in the segmentation anyway. The blood flow through the stenosis can then still be estimated accurately by flow or impedance boundary conditions with a scaling law using the root diameter information.

Figure 6:
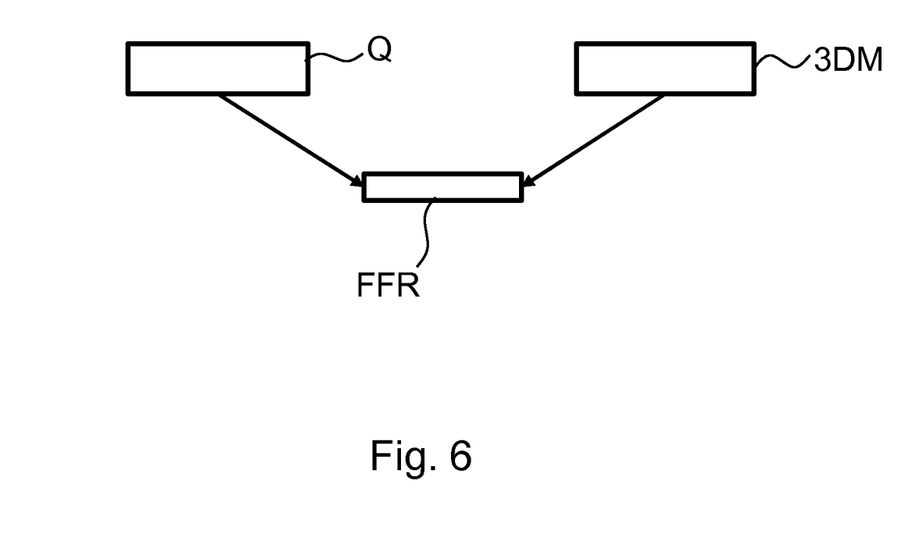
FIG. 6 shows a schematic diagram of a flowchart diagram for explaining the present invention.

FIG. 6 shows a schematic diagram of a flowchart diagram for explaining the present invention.

Initially, a three-dimensional model 3DM of an imaged vascular vessel tree VVT based on a partial segmentation of the imaged vascular vessel tree VVT surrounding a stenosed vessel segment SVS may be calculated.

Then, calculating a blood flow Q through the stenosed vessel segment SVS based on an analysis of a time-series of X-ray images may be performed.

Subsequently, a fractional flow reserve FFR based on the three-dimensional model 3DM and the calculated blood flow Q may be calculated.

Figure 7:
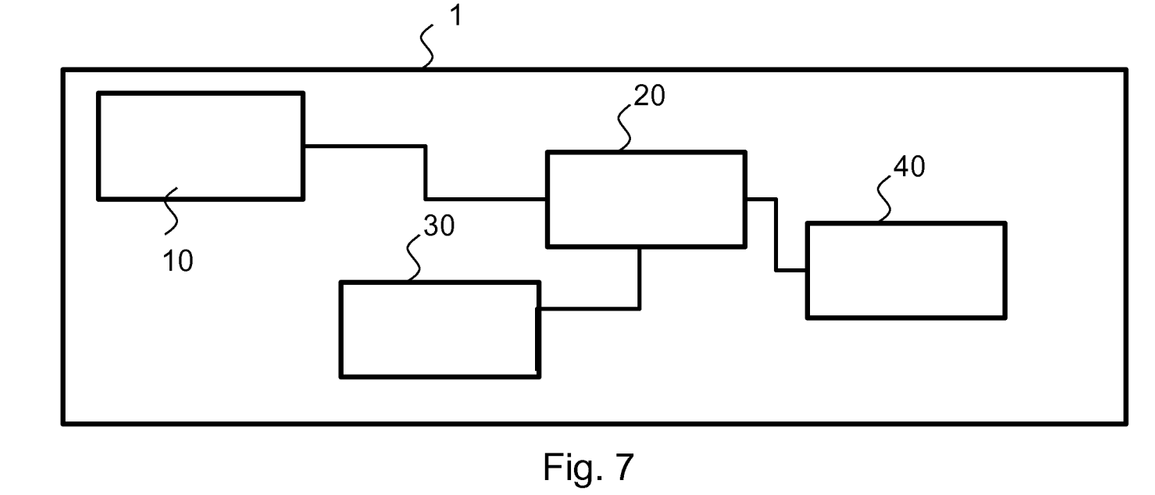
FIG. 7 shows a schematic diagram of a device for fractional flow reserve determination according to an exemplary embodiment of the present invention.

FIG. 7 shows a schematic diagram of a device 1 for fractional flow reserve determination.

The device 1 for fractional flow reserve determination may comprise a model generator 10, an image processor 20, and a fractional-flow-reserve determiner 30.

The model generator 10 may be configured to calculate a three-dimensional model 3DM of an imaged vascular vessel tree VVT on a partial segmentation of an image vascular vessel tree VVT surrounding a stenosed vessel segment SVS. The three-dimensional model may be a virtual structure of a vessel structure, a complex branched tree structure, or any other structure as a circuit, wherein the vessel structure is modeled by a plurality of tubes each of which defined by, for instance parameters like size, length, position, and direction.

The image processor 20 may be configured to calculate a blood flow Q through the stenosed vessel segment SVS based on an analysis of a time-series of X-ray images. The analysis may be an image processing analysis, for instance, a brightness analysis or an image contrast analysis.

The fractional-flow-reserve determiner 30 may be configured to determine a fractional flow reserve based on the three-dimensional model of the imaged vascular vessel tree VVT and the calculated blood flow Q.

Further, the distance between the location, at which the diameter of the ostium was measured, and the part, at which the segmentation of the stenosed vessel segment SVS starts, may be used as an input parameter by the model generator 10.

Figure 8:
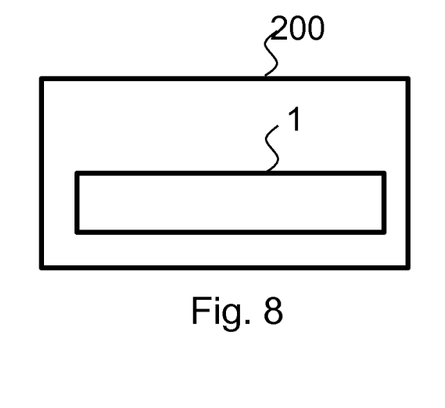
FIG. 8 shows a schematic diagram of a medical imaging device according to an exemplary embodiment of the present invention.

FIG. 8 shows a schematic diagram of a medical imaging system 200 according to an exemplary embodiment of the present invention.

The medical imaging system 200 may comprise an example of the device 1 for fractional flow reserve determination. The medical imaging system 200 may be an X-ray guided cardiac medical intervention device, a CT-imaging system or a magnetic resonance (MR) angiography imaging system.

Further, the medical imaging system 200 may be used for coronary flow reserve determination.

Figure 9:
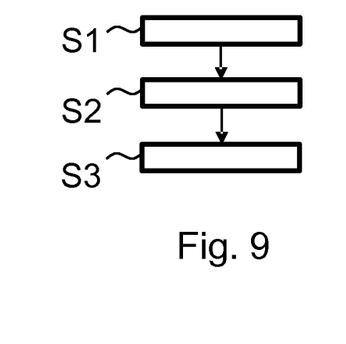
FIG. 9 shows a schematic diagram of a flowchart diagram of a method for fractional flow reserve determination according to an exemplary embodiment of the present invention.

FIG. 9 shows a schematic diagram of a flowchart of a method for fractional flow reserve determination. The method may comprise the following steps:

As a first step a) of the method, generating S1 a three-dimensional model of an imaged vascular vessel tree VVT based on a partial segmentation of the imaged vascular vessel tree VVT surrounding a stenosed vessel segment SVS by a model generator 10 may be conducted.

As a second step b) of the method, calculating S2 a blood flow Q through the stenosed vessel segment SVS based on an analysis of a time-series of X-ray images by image processor 20 may be conducted.

As a third step c) of the method, determining S3 a fractional flow reserve FFR based on the fractional flow reserve FFR and the calculated blood flow Q by a fractional-flow-reserve determiner 30 may be conducted.

According to an example, the step of calculating S2 the blood flow Q through the stenosed vessel segment SVS comprises calculating the blood flow Q using calibrated intensities over a region of interest including the stenosed vessel segment SVS. In an example, the step of determining S3 the fractional flow reserve FFR is performed using at least one boundary condition on an inlet and/or an outlet of the imaged vascular vessel tree VVT.

It has to be noted that embodiments of the present invention are described with reference to different subject-matters. In particular, some embodiments are described with reference to method type claims whereas other embodiments are described with reference to device type claims.

However, a person skilled in the art will gather from the above and the foregoing description that, unless otherwise notified, in addition to any combination of features belonging to one type of the subject-matter also any combination between features relating to different subject-matters is considered to be disclosed with this application.

However, all features can be combined providing synergetic effects that are more than the simple summation of these features.

While the present invention has been illustrated and described in detail in the drawings and the foregoing description, such illustration and description are to be considered illustrative or exemplary and not restrictive; the present invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for fractional flow reserve determination, the device comprising:
a processor configured to:
generate a three-dimensional model of a portion of an imaged vascular vessel tree surrounding a stenosed vessel segment, the imaged vascular vessel tree comprising one or more branches proximal to the stenosed vessel segment and one or more branches distal to the stenosed vessel segment, wherein the processor is configured to generate the three dimensional model based on a segmentation of only the stenosed vessel segment and the one or more branches distal to the stenosed vessel segment;
calculate a blood flow rate through the stenosed vessel segment based on an analysis of a time-series of X-ray images of the vascular vessel tree, wherein the analysis includes:
calibrating the time-series of X-ray images, wherein the calibrating comprises:
removing scatter and background structures from the time-series of X-ray images; and
calibrating an intensity of the time-series of X-ray images based on at least one of a phantom with a known attenuation or information associated with the three-dimensional model;
determining a curve representative of the intensity over time in the calibrated time-series of X-ray images; and
determining, as the blood flow rate, a slope of the curve at a time of contrast bolus arrival at only a region distal to the stenosed vessel segment;
determine a fractional flow reserve based on the three-dimensional model and the blood flow rate; and
output the fractional flow reserve for display at a display device in communication with the processor.

2. Device according to claim 1, wherein the processor is further configured to:
conduct the analysis of the time-series of X-ray images over a period comprising at least one of up to 12 s, up to 5 s, or up to 1 s.

3. Device according to claim 1,
further comprising a controllable injector, configured to provide a predefined flow profile of a contrast agent injected into the vascular vessel tree.

4. Device according to claim 1,
wherein the processor is configured to remove the scatter and background structures by i) top-hat filtering, or by ii) bone removal, or by iii) digital subtraction of a reference image in at least one image of the time-series of X-ray images or in an image recorded prior to the recording of the time-series of X-ray images.

5. Device according to claim 1,
wherein the processor is configured to calculate the fractional flow reserve using at least one boundary condition at an inlet and/or an outlet of the imaged vascular vessel tree.

6. Device according to claim 5,
wherein the processor is configured to use as the at least one boundary condition a pressure or flow constraint or a lumped element model composed of a resistor, a varistor or a capacitor.

7. Device according to claim 6,
wherein the processor is configured to use an aortic pressure measurement as basis for the pressure constraint used as the at least one boundary condition.

8. Device according to claim 5,
wherein the processor is configured to adjust the at least one boundary condition based on a determined diameter of a vessel of the imaged vascular vessel tree.

9. Device according to claim 8,
wherein the processor is configured to determine a coronary ostium diameter measurement as the determined diameter of the vessel of the imaged vascular vessel tree for adjusting the at least one boundary condition.

10. Device according to claim 5,
wherein the processor is configured to calculate a distal pressure of the stenosed vessel segment using a three-dimensional fluid dynamics simulation or a lumped components model, wherein a resistance of the stenosed vessel segment is approximated from a cross-sectional area of the stenosed vessel segment.

11. Device according to claim 1,
wherein the processor is configured to generate the three-dimensional model of the portion of the imaged vascular vessel tree based on a portion of the vascular vessel tree distal to the stenosed vessel segment.

12. A medical imaging system comprising:
the display device; and
a device according to claim 1,
wherein the display device is configured to display the determined fractional flow reserve.

13. Device according to claim 1, wherein the analysis further includes calculating the blood flow rate using at least one of a contrast transit time to the stenosed vessel segment or contrast arrival time at the stenosed vessel segment.

14. A method for fractional flow reserve determination, the method comprising the steps of:
generating a three-dimensional model of an imaged vascular vessel tree surrounding a stenosed vessel segment by a processor, based on a segmentation of only the stenosed vessel segment and one or more branches distal to the stenosed vessel segment of the imaged vascular vessel tree, the vascular vessel tree comprising one or more branches proximal to the stenosed vessel segment and the one or more branches distal to the stenosed vessel segment;
calculating a blood flow rate through the stenosed vessel segment based on an analysis of a time-series of X-ray images of the vascular vessel tree by the processor, wherein the analysis includes:
calibrating the time-series of X-ray images, wherein the calibrating comprises:
removing scatter and background structures from the time-series of X-ray images; and
calibrating an intensity of the time-series of X-ray images based on at least one of a phantom with a known attenuation or information associated with the three-dimensional model;
determining a curve representative of the intensity over time in the calibrated time-series of X-ray images; and
determining, as the blood flow rate, a slope of the curve at a time of contrast bolus arrival at only a region distal to the stenosed vessel segment;
determining a fractional flow reserve based on the three-dimensional model and the calculated blood flow by the processor; and
outputting, by the processor, the fractional flow reserve for display at a display device in communication with the processor.

15. Method according to claim 14, further comprising calculating the fractional flow reserve using at least one boundary condition at an inlet or an outlet of the imaged vascular vessel tree.

16. Method according to claim 15, further comprising adjusting the at least one boundary condition based on a determined diameter of a vessel of the imaged vascular vessel tree.

17. Method according to claim 16, further comprising determining a coronary ostium diameter measurement as the determined diameter of the vessel of the imaged vascular vessel tree for adjusting the at least one boundary condition.

18. Method according to claim 14, further comprising displaying the determined fractional flow reserve on the display device.

\* \* \* \* \*